United States Patent [19]
Bakos et al.

[11] Patent Number: 5,008,440
[45] Date of Patent: Apr. 16, 1991

[54] HERBICIDE COMPOSITION

[75] Inventors: József Bakos; Bálint Heil; Imre Tóth; Béla Édes, all of Veszprém; István Gebhardt, Budapest; Ferenc Bihari, Budapest; Anna Durkó née Pónácz, Budapest; Gyula Eifert, Dunaharaszti; Jeno Király, Budapest; Éva Konok née Horváth, Budapest; László Lukács, Budapest; Ágnes Mészáros née Szekrényesi, Budapest; Béla Radvány, Budapest; Lajos Sárosi, Budapest, all of Hungary

[73] Assignee: Budapesti Vegyimuvek, Budapest, Hungary

[21] Appl. No.: 454,775

[22] Filed: Dec. 21, 1989

[30] Foreign Application Priority Data

Dec. 27, 1988 [HU] Hungary .............................. 6609/88

[51] Int. Cl.$^5$ .............................................. C07C 69/76
[52] U.S. Cl. ........................................ 560/65; 71/107; 71/108
[58] Field of Search ...................... 560/65; 71/107, 108

[56] References Cited

U.S. PATENT DOCUMENTS 3,957,852  5/1976  Fujikawa et al. ...................... 560/65

Primary Examiner—Paul J. Killos
Attorney, Agent, or Firm—Herbert Dubno; Jonathan Myers

[57] ABSTRACT

A herbicide composition, which comprises (S)-1'-methoxycarbonylethyl 2-bromo-5-(2-chloro-4-trifluoromethylphenoxy) benzoate or (S)-1'-ethoxycarbonylethyl 2-bromo-5-(2-chloro-4-trifluoromethylphenoxy)benzoate as active ingredient in an amount of 0.01 to 95.0% by weight together with one or more solid and/or liquid carriers, preferably grists of native or synthetic materials; and/or with inert solvents, preferably xylenes and/or cyclohexanone; and optionally with surface active agents, preferably anionic and/or nonionic emulsifying or dispersing agents.

6 Claims, No Drawings

HERBICIDE COMPOSITION

FIELD OF THE INVENTION

This invention relates to the herbicidally active (S)-1'-methoxycarbonylethyl 2-bromo-5-(2-chloro-4-trifluoromethylphenoxy)benzoate and (S)-1'-ethoxycarbonylethyl 2-bromo-5-(2-chloro-4-trifluoromethylphenoxy)benzoate, to herbicide compositions containing these compounds and to a process for the preparation of both active compounds (ingredients).

BACKGROUND OF THE INVENTION

In the German patent specification (DE-PS) No. 3,029,728, substituted diphenyl ether derivatives of the formula (1) are disclosed.

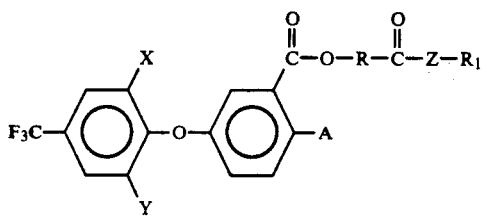

wherein
A stands for halogen or cyano group;
X stands for hydrogen or halogen;
Y is—among others—hydrogen or halogen;
Z stands for oxygen or sulfur;
R stands for—among others—a $C_{1-3}$alkylene group optionally substituted by a $C_{1-4}$alkyl group; and
$R_1$ stands for—among others—a $C_{1-10}$alkyl group.

In the German patent specification (DE-PS) No. 3,029,728, one single substance namely, (RS)-1'-ethoxycarbonylethyl 2-bromo-5-(2-chloro-4-trifluoromethylphenoxy)benzoate is published together with the description of its herbicidal activity. This compound is stated to be effective even in the half dose (140 g/ha) as compared to the known sec-butyl 5-(2-chloro-4-trifluoromethylphenoxy)-2-nitrobenzoate. However, no teaching (instruction) is given for the threshold value of the selectivity against cultivated plants.

No process for the preparation, physical and chemical characteristics as well as herbological properties of both compounds according to the present invention are defined in the patent specification cited above thus, these compounds have not been prepared and are therefore novel.

It is commonly known that a continuous social demand exists on novel compounds capable to inhibit the development of an undesired vegetation. The principal aim of the research consists in the selective inhibition of the development of weeds in the most frequent cases such as wheat, maize, rice, soy bean or cotton; namely, the uncontrolled growth of weeds is accompanied by a significant loss of production whereby the gain of the grower (farmer) is lowered and the expenses of the consumer become higher.

In the course of our herbological (plant protective) investigations it has been found that the compounds according to the present invention (compounds No. 1 and No. 2) possess a significantly higher herbicidal activity than that of (R)-antipodes (D and E) or that of (RS)-1'-methoxycarbonylethyl 2-bromo-5-(2-chloro-4-trifluoromethylphenoxy)benzoate (compound A) or that of (RS)-1'-ethoxycarbonylethyl 2-bromo-5-(2-chloro-4-trifluoromethylphenoxy)benzoate (compound B) described in the German patent specification No. 3,029,728 or that of (RS)-1'-ethoxycarbonylethyl 5-(2-chloro-4-trifluoromethylphenoxy)-2-nitrobenzoate (compound C) claimed in the published European patent application No. 0,020,052 A1. However, the selectivity threshold values of the compounds according to the present invention (compounds No. 1 and No. 2) are equal to those of the compounds A, B or C.

The herbicidal activity over 90% of the compounds No. 1 and No. 2 expressed in g/ha dose is surprisingly 3 to 17 times as high as that of the racemates A, B and C, and 4 to 22 times as high as that of the R-antipods D and E respectively (Table 1), a fact unexpected for one skilled in the art.

Further on, it is concluded from the equality of the selectivity threshold values (see Table 2) that compounds A B, C, D and E are phytotoxic, i.e. they are harmful to the cultivated plants in a dose killing the weeds (50 to 500 g/ha) since this dose is substantially higher than the selectivity threshold values (30 to 200 g/ha) of the cultivated plants. In contrast to the compounds A, B, C, D and E, both compounds according to the present invention can be used for killing the weeds in cultivated plants, too since their selectivity threshold value (50 to 180 g/ha) is a manyfold of the dose (10 to 40 g/ha) required to achieve a herbicidal efficiency over 90%.

By knowing the herbicidal activity and the selectivity threshold value of compounds No. 1 and No. 2 according to the present invention especially on the basis of the herbological behavior of the compounds A, B, C, D and E—it can be stated, that the outstanding herbicidal activity and selectivity threshold value of compounds No. 1 and No. 2 according to the present invention, furthermore the superior suitability of those compounds resulting from the interrelation of both above mentioned characteristics, which were unexpected for a person skilled in the art, have not been recognized during the investigation of compounds of similar structure.

Both compounds according to the invention can be prepared by using known methods, e.g. by (a) reacting the (5) enantiomer or racemate of a lactic acid ester of the Formula (I),

wherein R means a methyl or ethyl group, with an at least stoichiometric amount of a 2-bromo-5-(2-chloro-4-trifluoromethylphenoxy)benzoyl halide, preferably chloride, suitably in the presence of an acid binding agent; or (b) reacting the (S)-enantiomer or racemate of an alkyl 2-halopropionate or the formula (II)

wherein R stands for a methyl or ethyl group and Hal means chlorine or bromine, with 2-bromo-5-(2-chloro-4-trifluoromethylphenoxy)benzoic acid, preferably in the presence of an aza-compound, e.g. 1,5-diazabicyclo[5.4.0]-undec-5-ene (DBU) and resolving the product obtained when one of the reactants is a racemic compound.

Any inert solvent may be used in the above reactions. Suitable solvents are e.g.: pentane, hexane, heptane, cyclohexane petroleum ether, gasoline, ligroine, benzene, toluene, xylene, dichloromethane, dichloroethane, chloroform, carbon tetrachloride, chlorobenzene, o-dichlorobenzene, diethyl ether, dibutyl ether, ethylene glycol dimethyl ether, tetrahydrofuran, dioxane, acetone, methyl ethyl ketone, methyl isopropyl ketone, methyl isobutyl ketone, methyl acetate, ethylacetate, acetonitrile, propionitrile, dimethylformamide (DMF), N-methylpyrrolidone, dimethyl sulfoxide (DMSO), tetramethylene sulfone, hexamethylphosphoric acid triamide.

Hydroxides, hydrogen carbonates, carbonates and alkoxides of alkaline metals as well as aliphatic, aromatic or heterocyclic amines are useful acid binding agents.

According to a preferred embodiment of the process of the present invention, approximately equimolar amounts of the starting substances are reacted at a temperature between −20° C. and the boiling point of the reaction mixture. Preferably, a solution of 2-bromo-5-(2-chloro-4-trifluoromethylphenoxy)benzoic acid or 2-bromo-5-(2-chloro-4-trifluoromethylphenoxy)benzoyl chloride is portionwise added between −20° C. and 35° C. and after this addition, the reaction mixture is stirred under reflux up to the desired progress of the reaction (transformation). After cooling down, the solution is washed with dilute acid, then dilute base and water and the phases are separated. The product can be obtained in any known way, e.g. by evaporation.

The invention further relates to a herbicide composition containing (S)-1'-methoxycarbonylethyl 2-bromo-5-(2-chloro-4-trifluoromethylphenoxy)benzoate or (S)-1'-ethoxycarbonylethyl 2-bromo-5-(2-chloro-4-trifluoromethylphenoxy)benzoate as active ingredient in an amount of 0.01 to 95.0% by weight together with one of more solid and/or liquid carriers, preferably grists of native or synthetic materials; and/or with inert solvents, preferably xylenes and/or cyclohexanone; and optionally with surface active agents, preferably anionic and/or nonionic emulsifying or dispersing agents.

According to an other aspect of the invention, there is provided a process for the preparation of (S)-1'-methoxycarbonylethyl 2-bromo-5-(2-chloro-4-trifluoromethylphenoxy)benzoate or (S)-1'-ethoxycarbonylethyl 2-bromo-5-(2-chloro-4-trifluoromethylphenoxy)benzoate, i.e. for both compounds according to the invention, which comprises, reacting the (S) enantiomer of a lactic acid ester of the formula (I), wherein R stands for a methyl or ethyl group, with 2-bromo-5-(2-chloro-4-trifluoromethylphenoxy)benzoyl halide, preferably chloride in a solvent, preferably in the presence of an acid binding agent then separating the (5)-1'-methoxycarbonylethyl 2-bromo-5-(2-chloro-4-trifluoromethylphenoxy)benzoate or (5)-1'-ethoxycarbonylethyl 2-bromo-5-(2-chloro-4-trifluoromethylphenoxy)benzoate thus obtained from the reaction mixture, and if desired, purifying them.

The intermediates used in the synthesis of both compounds according to the invention are known compounds.

The synthesis of 2-bromo-5-(2-chloro-4-trifluoromethylphenoxy)benzoic acid and its halide is described in the U.S. Pat. No. 3,957,852. (RS)- and (S)-lactic acid, their methyl and ethyl esters as well as the methyl and ethyl esters of (RS)-2-halopropionates are commercially available.

The preparation of (RS)-1'-ethoxycarbonylethyl 2-bromo-5-(2-chloro-4-trifluoromethylphenoxy)benzoate used as reference compound (standard) is published in the German patent specification No. 3,029,728; (RS)-1'-methoxycarbonylethyl 2-bromo-5-(2-chloro-4-trifluoromethylphenoxy)benzoate was synthetized in an analogous manner, except that methyl (RS)-lactate was used instead of ethyl (RS)-lactate.

The compositions according to the invention are used (applied) preemergently or, more preferably, in a postemergent manner. The dose of the active ingredient may be varied from 10 to 100, preferably from 10 to 75 g/ha dependently on the quality of the soil, weather conditions, components of the weed flora and the like. 50 to 1000 liters/hectare (hereinafter abbreviated l/ha), preferably 50 to 500 l/ha of spray liquid may be used.

The compounds according to the invention (active ingredients) can be formulated in the usual forms by methods known per se. Thus, e.g. wettable powders (WP), suspension concentrates (SC), water-miscible solution concentrates (SL), emulsifiable concentrates (EC), granules applicable without water (S), dusting powders (DP) or oily suspension concentrates (FO) may be prepared. The active ingredient mixtures can be applied in ULV forms as well. In the said compositions, the mixture of the active ingredients is present in an admixture with solid or liquid carriers or diluents and optionally with other auxiliary agents. The said auxiliary agents may be e.g. surfactants, wetting agents, suspending agent, dispersing agents, emulsifiers, anti-agglomerating agents, anti-caking agents, adhesive agents, spreaders, penetration increasing agents, substances capable of maintaining or increasing the biological activity, antifoam agents etc. From the group of solid carriers and diluents, the following substances can be mentioned: inactive minerals e.g. Kaolin (China-clay), various Kaolin types, attapulgite, montmorillonite, mica slate, pyrophillite, bentonite, diatomaceous earth or highly dispersed synthetic silicic acids, calcium carbonate, calcinated magnesium oxide, dolomite, gypsum, tricalcium phosphate, Fuller's earth. Suitable further solid carriers and diluents are ground tobacco leaf stem, wood flour etc.

Suitable liquid diluents and solvents are the following materials: water; organic solvents; mixtures of organic solvents and those formed with water e.g. methanol, ethanol, n-propanol, isopropanol, diacetone alcohol, benzyl alcohol; esters of the said alcohols e.g. methyl cellosolve; ketones e.g. dimethyl ketone, methyl ethyl ketone, methyl isobutyl ketone, cyclopentanone, cyclohexanon etc.; ethyl acetate, n- and isobutyl acetate, amyl acetate, isopropyl myristate, dioctyl phthalate, dihexyl phthalate etc.; aromatic, aliphatic and alicyclic hydrocarbons e.g. paraffine hydrocarbons, cyclohexane, kerosene, gasoline, benzene, toluene, xylene, tetraline, decaline etc.; mixtures of alkyl benzenes; chlorinated hydrocarbons e.g. trichloroethane, dichloromethane, perchloroethylene, dichloropropane, chlorobenzene etc.; lactones e.g. γ-butyrolactone etc.; lactams e.g. N-methylpyrrolidone, N-cyclohexylpyrrolidone; acid amides e.g. dimethylformamide and the like; oils of vegetable or animal origin e.g. sunflower oil, olive oil, soya oil, castor oil and the like.

The suitable wetting, dispersing, emulsifying, adhesive, anti-aggregating, anti-caking and spreading agents may be of ionic or non-ionic character. The ionic surfactants may be e.g. salts of various saturated of unsaturated carboxylic acids; sulfonates of aliphatic, aromatic or arylaliphatic hydrocarbons; sulfates of alkyl, aryl of aralkyl alcohols; sulfonates of alkyl, aryl of aralkyl acids, esters and ethers; sulfonates of condensation products of phenol, cresol and naphthalene; sulfated vegetable and animal oils; alkyl, aryl and aralkyl phosphate esters; salts of the above compounds formed with alkaline or alkaline earth metals or organic bases (e.g. various amines, alkanolamines and the like). As preferred representatives of the above surfactants, the following compounds may be mentioned: sodium lauryl sulfate, sodium 2-ethylhexylsulfate sodium ethanolamine, diethanolamine, triethanolamine, and isopropylamine salt of dodecylbenzenesulfonic acid; sodium mono- and diisopropylnaphthalene sulfonate; sodium salt of naphtalenesulfonic acid, sodium diisooctylsulfosuccinate; sodium xylenesulfonate; sodium or calcium salt of petroleumsulfonic acid; soaps; potassium, sodium, calcium, aluminum, magnesium stearate and the like. The phosphate esters may be e.g. ethers of phosphatized alkyl phenols or fatty alcohols formed with polyglycols and forms thereof partially or completely neutralized with the cations or organic bases mentioned above. As further suitable representatives of anionic surfactants, disodium N-octadecylsulfosuccinate, sodium N-oleyl-N-methyl-tauride and various ligninesulfonates can be mentioned.

Suitable non-ionic wetting, dispersing and emulsifying agents are the ethers of ethylene oxide formed with $C_{10-20}$ alcohols, e.g. stearyl polyoxyethylene, oleyl polyoxyethylene and the like; ethers formed with alkylphenols e.g. polyglycol ethers formed with tertiary butyl-, octyl- and nonylphenol etc.; esters of various acids e.g. polyethylene glycol ester of stearic acid or myristic acid or polyethylene glycol oleate etc.; block polymers of ethylene oxide and propylene oxide; partial esters of fatty and oleic acids formed with hexitol anhydrides; esters of sorbitol formed with oleic acid or stearic acid; condensation products of the above compounds formed with ethylene oxide; tertiary glycols e.g. 3,6-dimethyl-4-octyne-3,6-diol or 4,7-dimethyl-5-decyne-4,7-diol; polyethylene glycol thioethers e.g. ester of dodecyl mercaptan formed with polyethylene glycol etc.

As adhesive agents, e.g. alkaline earth metal soaps; salts of sulfosuccinic acid ester; natural or artificial, water-soluble macromolecules e.g. casein, starch, Arabian gum, cellulose ethers, methylcellulose, hydroxycellulose, polyvinylpyrrolidone and polyvinyl alcohol etc. may be used.

Suitable antifoam agents are lower polyoxyethylene and polyoxypropylene block polymers (wherein the number of octyl-, nonyl- and phenylpolyoxyethylene/ethylene oxide units is $>5$); long-chain alcohols e.g. octyl alcohol, special silicone oils etc, By using suitable additives, formulated compositions of the present invention can be made colloid-chemically compatible with various fertilizers.

The selective herbicidal compositions of the present invention may comprise known pesticides and/or nutritive components, if necessary.

Wettable powders (WP) can be prepared e.g. by mixing the active ingredients, auxiliary agents and surfactants with the carriers, then grinding and finally homogenizing the mixture. Liquid surfactants may be applied e.g. by spraying them on the solid organic of inorganic carriers or onto a powder mixture comprising the solid active ingredient. When a liquid surfactant is used, the previously ground solid components may be suspended in an organic solvent comprising liquid surfactants. This suspension can be dried e.g. by pulverization. Thus, the surfactant is applied onto the surface of a mixture of the solid active ingredient and the solid diluent.

A self-emulsifiable liquid, suitable for the preparation of aqueous dispersed emulsions (so-called emulsifiable concentrate EC) can be prepared by dissolving the active ingredient or a mixture thereof in a water-immiscible solvent. The emulsifiable concentrate thus obtained forms with water spontaneously or under slight mechanical effect a spray emulsion which remains unchanged and stable even after a long storage.

A water-soluble solution concentrate (SL) can be prepared by dissolving the active ingredient and the suitable water-soluble auxiliary materials (additives) in water and/or in a water-miscible solvent. After diluting with water, a spray liquid with the desired concentration can be obtained. The aqueous solution concentrate of the active ingredient may be dispersed also in a water-immiscible liquid by choosing (selecting) a suitable emulsifying agent to obtain a so-called "inverse" emulsion. Thus, by the convenient selection of the solvent and surface active agents such compositions can be prepared which, on the effect of mixing with water or water-immiscible liquids, result in even molecularly dispersed phases remaining unchanged even after a long storage time.

A suspension concentrate (SC) can be prepared by dissolving the wetting and dispersing agents in a mixture of water (preferably ion-exchanged water) and an antifoam component (preferably ethylene glycol or glycerol), is necessary under warming. To the solution thus obtained a mixture of the solid (powdered or crystalline) active ingredients is added under continuous stirring and, if desired, an anti-caking component is added. The slurry thus obtained (solid particles—liquid phase) is ground in a wet mill (e.g. a closed Dyno mill) to the desired particle size, preferably to a maximum particle size of 5 $\mu$m. After grinding, an antifoam agent and a thickening component are added under homogenization. Alternatively, the order of succession of the addition of the components may be changed of further agents (e.g. dyes) may be added. In addition to said active ingredients other active ingredients can be added as well. Solid active ingredients having a low melting point may also be introduced in the form of a melt without or together with an emulsifier.

ULV compositions can be formulated similarly to EC (or in certain cases to SC) compositions.

Granules suitable for direct use (G) can be prepared by extrusion, lamination, by applying onto a granular carrier (e.g. ground limestone) or by absorbing a liquid component in a carrier having sorption capacity.

Granules applicable for spraying purposes (WG) can be prepared starting from WP and/or SC with the aid of an agglomeration technology e.g. in a dragée pan by using a binding agent.

A spray or dusting powder suitable for use in agriculture can be obtained from the above compositions by known methods by dilution with water or an inert solid carrier. The active ingredient content of the said ready-for-use compositions is generally below 5% by weight, preferably 0.01–3% by weight.

In the compositions to be used (applied), the amount of the active ingredient may be varied between wide limits; its value essentially depends on the effect desired.

The invention is illustrated in detail by the following non-limiting Examples.

In the $^1$H-NMR and $^{13}$C-NMR spectroscopic data given in the Examples, the identification method indicated in the formula (III)

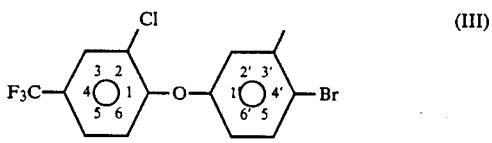

was used. Although this is different from the indication according to the nomenclature, however, it makes possible to carry out an uniform spectroscopic evaluation.

EXAMPLE 1

Preparation of (S)-1'-methoxycarbonylethyl 2-bromo-5-(2-chloro-4-trifluoromethylphenoxy)benzoate (compound No. 1)

100 ml of benzene, 28.6 g (0.2747 mol) of methyl (S)-lactate [[α]$_D^{20}$= −8.97° (neat)] and 22.3 ml (0.2747 mol) of anhydrous pyridine are weighed in a three-necked flash equipped with a stirrer, dropping funnel and reflux condenser. The mixture is cooled to 10° C. and a solution containing 113.7 g (0.2747 mol) of 2-bromo-5-(2-chloro-4-trifluoromethylphenoxy)benzoyl chloride in 100 ml of benzene is dropwise added under vigorous stirring at such a rate that the temperature of the reaction mixture remains between 10° and 20° C. under an external cooling. After this addition, the suspension is stirred at 20° to 30° C. for additional 10 hours and then poured onto 300 ml of 3% hydrochloric acid. After separating, the organic phase is successively washed with 200 ml of 3% sodium hydrogen carbonate solution saturated with sodium chloride and then with 200 ml of saturated aqueous sodium chloride solution. After drying the benzene solution over anhydrous magnesium sulfate, the solvent is evaporated under atmospheric pressure and then under the water jet pump. The named compound is obtained as a pale yellow, oily product in a yield of 110.2 g (92.7%).

Molecular weight: 481.4.
Color and form: pale yellow oil.
[α]$_D^{20}$= +9.21° (c 7.385, benzene).
n$_D^{20}$=1.5424.

The characteristic fragments of the mass spectrum of the named product show the isotopic ratio characteristic of compounds containing one chlorine and one bromine atom.

m/e(r.i.)=482 (280)=F$_3$C(Cl)C$_6$H$_3$OC$_6$H$_3$(Br)COOCH(CH$_3$)COOCH$_3$; 480 (210)=F$_3$C(Cl)C$_6$H$_3$OC$_6$H$_3$(Br)COOCH(CH$_3$)COOCH$_3$; 381 (230)=F$_3$C(Cl)C$_6$H$_3$OC$_6$H$_3$(Br)CO; 379 (1000)=F$_3$C(Cl)C$_6$H$_3$OC$_6$H$_3$(Br)CO; 377 (710)=F$_3$C(Cl)C$_6$H$_3$OC$_6$H$_3$(Br)CO;

$^1$H-NMR(CDCl$_3$): δ 1,52(d, 3H), 3,65 (s, 3H), 5,22 (q, 1H), 6,77–7,63 ppm (complex m, 6H).

$^{13}$C-NMR(CDCl$_3$): δ 155,0(s, C-1), 126,2(s, C-2), 128,4(q, $^3$J(FCCC)=3,6 Hz, C-3), 125,6(q, $^3$J(FCCC)=3,6 Hz), 120,1 (s, C-6), 155,0(s, C-1'), 122,1(s, C-2'), 136,1(s, C-3'), 116,6(s, C-4'), 133,1(s, C-5'), 123,1(s, C-6'), 170,7(s, COOCH$_3$), 164,4(s, COOCH$_3$), 52,4(s, OCH$_3$), 16,9(s, CH$_3$), 70,0 ppm (s,CH).

EXAMPLE 2

Preparation of (S)-1'-ethoxycarbonylethyl 2-bromo-5-(2-chloro-4-trifluoromethylphenoxy)benzoate (compound No. 2)

100 ml of benzene, 10.1 ml (0.1252 mol) of anhydrous pyridine and 14.3 ml (0.1252 mol) of ethyl (S)-lactate [[α]$_D^{20}$= −12° (neat)] are weighed in a three-tube bottle equipped with a stirrer, dropping funnel and reflux condenser. After cooling the homogeneous solution to 10° C., a solution containing 51.8 g (0.1252 mol) of 2-bromo-5-(2-chloro-4-trifluoromethylphenoxy)benzoyl chloride in 100 ml of benzene is dropwise added under stirring and external cooling to maintain the temperature of the reaction mixture at 10° to 20° C. Then, the suspension is heated to the boiling point and refluxed at the same temperature for 6 hours while stirring. After cooling down, 200 ml of 3% hydrochloric acid are poured to the reaction mixture. After stirring for a short time, the organic phase is separated and successively washed with 150 ml of 3% sodium hydrogen carbonate solution saturated with sodium chloride, then with 150 ml of an aqueous saturated sodium chloride solution. After drying the benzene solution over anhydrous magnesium sulfate, the solvent is evaporated first under atmospheric pressure and then under pressure of the water jet pump. The named compound is obtained as a pale yellow oily product in a yield of 55.6 g (89.4%).

Molecular weight: 495.4.
Color and form: pale yellow oil.
[α]$_D^{20}$= +7.77° (c 5.66, benzene).
n$_D^{20}$=1.5324.

The characteristic fragments of the mass spectrum of the named compound show the isotopic ratio characterizing compounds containing one chlorine and one bromine atom.

m/e(r.i.)=496 (230)=F$_3$C(Cl)C$_6$H$_3$OC$_6$H$_3$(Br)COOCH(CH$_3$)COOC$_2$H$_5$; 494 (180)=F$_3$C(Cl)C$_6$H$_3$OC$_6$H$_3$(Br)COOCH(CH$_3$)COOC$_2$H$_5$; 381 (260)=F$_3$C(Cl)C$_6$H$_3$OC$_6$H$_3$BrCO, 379 (1000)=F$_3$C(Cl)C$_6$H$_3$OC$_6$H$_3$BrCO, 377 (710)=F$_3$C(Cl)C$_6$H$_3$OC$_6$H$_3$BrCO.

$^1$H-NMR(CDCl$_3$): δ 1,23 (t, 3H), 1,55 (d, 3H), 4,16 (q, 2H), 5,24 (q, 1H), 6,85–7,2 ppm (complex m, 6H).

$^{13}$C-NMR(CDCl$_3$): δ 155, 0 (S, C-1), 126,2 (S, C-2), 128,5 (9, J(FCCC)=3,6 Hz, C-3), 125,6 (q, J(FCCC)=3,6 Hz, C-5), 120,1 (s, C-6), 155,0 (s, C-1'), 122,0 (s, C-2'), 136,1 (s, C-3'), 116,5 (s, C-4'), 133,3 (s, C-5'), 123,1 (s, C-6'), 170,2 (s, COOCH), 164,5 (s, COOC$_2$H$_5$), 61,6 (s, OCH$_2$), 14,1 (s, CH$_3$CH$_2$), 16,9 (s, CH$_3$), 70,1 ppm (s, CH).

EXAMPLE 3

Preparation of (R)-1'-methoxycarbonyl ethyl-2-bromo-5-(2-chloro-4-trifluoromethylphenoxy)-benzoate (compound D)

This compound was prepared following substantially the procedure of Example 1 using methyl (R)-lactate instead of methyl (S)-lactate at a yield of 92.7%.

Molecular weight: 481,4.
Colour and form: pale yellow oil.
[α]$_D^{20}$= −7.83° (c 4.91, benzene).
n$_D^{20}$=1.5424.

The characteristic fragments of the mass spectrum of the named product, the data of the $^1$H- and $^{13}$C-NMR spectra correspond to those of the (S)-enantiomer obtained in Example 1.

EXAMPLE 4

Preparation of (R)-1'-ethoxycarbonylethyl-2-5-(2-chloro-4-trifluoromethylphenoxy)bromo benzoate (compound E)

This compound was prepared following substantially the procedure given in Example 2 using ethyl (R)-lactate instead of ethyl (S)-lactate at a yield of 88.7%.

Molecular weight: 495,4.
Colour and form: yellow oil.
$[\alpha]_D^{20} = -7.70°$ (c 4.96, benzene).
$n_D^{20} = 1.5352$.

The characteristic fragments of the mass spectrum of the named product, the data of the $^1H$ and $^{13}C$-NMR spectra correspond to those of the (S)-enantiomer obtained in Example 2.

EXAMPLE 5

(a) Preparation of an emulsifiable concentrate (20 EC)

|  | % by weight |
|---|---|
| Compound No. 2 | 20 |
| 2-Ethoxyethanol | 10 |
| Cyclohexanone | 35 |
| Emulsogen EL 360 (1) | 7 |
| Tensiofix CD 5 (2) | 3 |
| Xylene | 25 |

(1) Ethoxylated castor oil
(2) Ethoxylated coconut alcohol

Emulsogen EL 360 and Tensiofix CD 5 are dissolved in the mixture of 2-ethoxyethanol, cyclohexanone and xylene and finally, the compound No. 2 is introduced to the system, then the solution is stirred for 2 hours. Compositions containing the compound No. 1., compounds A, B, C, D and E may similarly be prepared.

(b) Preparation of an emulsifiable concentrate (35 EC)

|  | % by weight |
|---|---|
| Compound No. 1 | 35 |
| Cyclohexanone | 10 |
| Tensiofix CD 21 (1) | 2 |
| Tensiofix B 7453 (2) | 8 |
| Xylene | 45 |

(1) A mixture of ethoxylated fatty alcohol, ethoxylated nonylphenol and their phosphates
(2) A solution of calcium dodecylbenzenesulfonate, ethoxylated nonylphenol and ethoxylated-propoxylated nonylphenol in n-butanol The process described under a) is followed.
Compositions containing the compound No. 2., compounds A, B, C, D and E may similarly be prepared.

EXAMPLE 6

Preparation of microgranules

|  | % by weight |
|---|---|
| Compound No. 2 | 0.1 |
| Cyclohexanone | 5.0 |
| Bentonite | 94.9 |

A solution containing the compound No. 2 in cyclohexanone is sprayed onto bentonite previously ground to a particle size of 50μ and placed in a revolving drum. The stirring is continued for 1 hour while cyclohexanone is evaporated.

A composition containing the compound No. 1., compounds A, B, C, D and E may similarly be prepared.

EXAMPLE 7

Preparation of water-dispersible grounds (WG)

|  | % by weight |
|---|---|
| Compound No. 1 | 50 |
| Cab-O-Sil M5 (1) | 5 |
| Atlox 4862 (2) | 3 |
| Polifon O (3) | 6 |
| Geropon IN (4) | 5 |
| Kaolin | 31 |

(1) Amorphous silicon dioxide
(2) Naphthalenesulfonate-formaldehyde condensation product
(3) Binding material (sodium ligninsulfonate)
(4) Isopropyl napthelenesulfonate The active ingredient is mixed in a grinding mortar with amorphous silicon dioxide, Atlox 4862 dispersing agent and Geropon IN wetting agent as well as kaolin. The mixture is ground to fine particles (until reaching that the portion of the particles higher than 44μ in diameter becomes lower than 0.5%). The powder is mixed in a kneader with the aqueous solution of the Polifon O binding agent and then granules of 1 mm in diameter are prepared in an extruder. The granules are dried in air stream.

A composition containing the compound No. 2., compounds A, B, C, D and E may similarly be prepared.

EXAMPLE 8

Biological (herbological) investigations

The herbicidal activity and selectivity of the compounds according to the invention were compared to the structurally related (R)-antipode (compound D) and (RS)-1'-methoxycarbonylethyl 2-bromo-5-(2-chloro-4-trifluoromethylphenoxy)benzoate (compound A) as well as (R)-antipode (compound E) and (RS)-1'-ethoxycarbonylethyl 2-bromo-5-(2-chloro-4-trifluoromethylphenoxy)benzoate (compound B) and to the commercially available (RS)-1'-ethoxycarbonylethyl 5-(2-chloro-4-trifluoromethylphenoxy)-2-nitrobenzoate (compound C) as reference (standard) substances.

Depending on the plant species, an equal number (20 to 50) of grains each were sowed in plastic cultivating bottles to a depth of 0.5 cm, then the soil was sprinkled when necessary and the bottles were maintained under the optimum temperature and light conditions. After the weeds had reached a real 2 to 4-leaf phase or the cultivated plants had been in a 3 to 6-leaf phase, respectively the spraying was carried out with 5, 15, 45, 135, 405 or 1215 g/ha dose, respectively of the active ingredient. The evaluation was made on the 10th day after the treatment by measuring the percentage of perishment (L. Bánki: Bioassay of Pesticides in the Laboratory, Akadémiai Kiadó, Budapest, Hungary, 1978) and determining therefrom the doses required for a perishment over 90% by using the probit analysis (D. J. Finney: Probit Analysis, Cambridge University Press, 2nd Ed. 1964). Simultaneously, the selectivity threshold values of the cultivated plants, i.e. the highest doses tolerated by the plants without any damage, were determined. The results are summarized in Table 1 and 2.

Abbreviations used in the tables are as follows:
(a) *Amarantus retroflexus* (pilous amaranth)
(b) *Solanum nigrum* (black nightshade)
(c) *Portulaca oleraceae* (fatty purslane)
(d) *Matricaria inodora* (scentless matricaria)
(e) *Datura stramonium* (medicinal nightshade)
(f) *Chenopodium album* (white goose-foot)
(g) *Oryza sativa* (rice)
(h) *Triticum vulgare* (winter wheat)
(i) *Hordeum vulgare* (winter barley)
(j) *Glycine soja* (soy bean)

TABLE 1

| No. or Symbol of the compound | R | Config-uration | Doses required to a herbicidal activity over 90% (g/ha) | | | | | |
|---|---|---|---|---|---|---|---|---|
| | | | a | b | c | d | e | f |
| 1. | Me | S | 10 | 15 | 15 | 20 | 25 | 30 |
| 2. | Et | S | 15 | 20 | 20 | 25 | 40 | 30 |
| Compound A | Me | RS | 45 | 45 | 45 | 100 | 180 | 450 |
| Compound B | Et | RS | 50 | 100 | 55 | 120 | 200 | 500 |
| Compound C | Et | RS | 50 | 100 | 50 | 130 | 250 | 500 |
| Compound D | Me | R | 100 | 120 | 70 | 140 | 270 | 600 |
| Compound E | Et | R | 120 | 120 | 65 | 130 | 240 | 550 |

TABLE 2

| No. or symbol of the compound | R | Configu-ration | Selectivity threshold values g/ha | | | |
|---|---|---|---|---|---|---|
| | | | g | h | i | j |
| 1. | Me | S | 150 | 70 | 50 | 50 |
| 2. | Et | S | 180 | 70 | 50 | 50 |
| Compound A | Me | RS | 150 | 50 | 70 | 60 |
| Compound B | Et | RS | 190 | 50 | 60 | 60 |
| Compound C | Et | RS | 150 | 75 | 50 | 30 |
| Compound D | Me | R | 150 | 70 | 70 | 60 |
| Compound E | Et | R | 180 | 70 | 60 | 60 |

EXAMPLE 9

Field experiments

These investigations were carried out by using the compounds No. 1 and No. 2, respectively according to the invention and the reference compounds A, B, C, D and E, respectively on winter wheat of the Aurora species on parcels of 20 m² in four repetitions. The compounds used in these experiments were formulated as described under (a) in Example 5. The weeds occurring in the areas indicated were: *Anthemis arvensis, Convolvulus arvensis, Matricaria inodora, Veronica hederifolia* and *Stellaria media*. The spraying was carried out on March 23, when *Stellaria media* reached the beginning of the blooming and other weeds were in a development phase of at most 10 cm. The herbicidal activity of the compositions was evaluated at the end of the 3rd week after the spraying (L. Bánki: Bioassay of Pesticides in the Laboratory, Akadémiai Kiadó, Budapest, Hungary, 1978). Except for *Stellaria media*, 100% of the weeds were killed in all treatments. An important difference concerning the herbicidal activity on *Stellaria media* was observed between the compounds according to the invention and the reference compounds. *Stellaria media* was advantageously killed by the compounds according to the invention whilst the reference substances were inactive. The covering by *Stellaria media* of the fields treated by a 50 g/ha dose of the reference substances reached 50%. A considerable difference exists between the phytotoxicity against the winter wheat of the compounds according to the invention and that of the reference compounds.

The data obtained on winter wheat and *Stellaria media* are summarized in Table 3.

TABLE 3

| No. or symbol of the compound | Dose g/ha | R | Configuration | Perishment % | |
|---|---|---|---|---|---|
| | | | | Winter wheat | Stellaria media |
| 1. | 25 | Me | S | 0 | 80 |
| | 50 | | | 0 | 100 |
| | 100 | | | 0 | 100 |
| 2. | 25 | Et | S | 0 | 80 |
| | 50 | | | 0 | 100 |
| | 100 | | | 0 | 100 |
| Compound A | 25 | Me | RS | 0 | 0 |
| | 50 | | | 0 | 0 |
| | 100 | | | 15 | 0 |
| Compound B | 25 | Et | RS | 0 | 0 |
| | 50 | | | 0 | 0 |
| | 100 | | | 15 | 0 |
| Compound C | 25 | Et | RS | 0 | 0 |
| | 50 | | | 0 | 0 |
| | 100 | | | 10 | 0 |
| Compound D | 25 | Me | R | 0 | 0 |
| | 50 | | | 0 | 0 |
| | 100 | | | 20 | 0 |
| Compound E | 25 | Et | R | 0 | 0 |
| | 50 | | | 0 | 0 |
| | 100 | | | 25 | 0 |

We claim:

1. (S)-1'-Methoxycarbonylethyl 2-bromo-5-(2-chloro-4-trifluoromethylphenoxy)benzoate.

2. (S)-1'-Ethoxycarbonylethyl 2-bromo-5-(2-chloro-4-trifluoromethylphenoxy)benzoate.

3. A herbicide composition, which comprises (S)-1'-methoxycarbonylethyl 2-bromo-5-(2-chloro-4-trifluoromethylphenoxy)benzoate or (S)-1'-ethoxycarbonylethyl 2-bromo-5-(2-chloro-4-trifluoromethylphenoxy)benzoate as active ingredient in an amount of 0.01 to 95.0% by weight together with at least one agriculturally acceptable inert carrier.

4. A composition as claimed in claim 3, which comprises (S)-1'-methoxycarbonylethyl 2-bromo-5-(2-chloro-4-trifluoromethylphenoxy)benzoate as active ingredient.

5. A composition as claimed in claim 3, which comprises (S)-1'-ethoxycarbonylethyl 2-bromo-5-(2-chloro-4-trifluoromethylphenoxy)benzoate as active ingredient.

6. A method of controlling undesired weed growth comprising applying a herbicidally effective composition as defined in claim 3.

* * * * *